US006096946A

United States Patent [19]
Roberts et al.

[11] Patent Number: 6,096,946
[45] Date of Patent: Aug. 1, 2000

[54] CONTROL OF POD DEHISCENCE

[75] Inventors: Jeremy Alan Roberts, Hathern, United Kingdom; Simon Allan Coupe, Palmerston North, New Zealand; Elizabeth Sarah Jenkins, Beeston, United Kingdom

[73] Assignee: Biogemma UK Limited, Cambridge, United Kingdom

[21] Appl. No.: 08/941,532

[22] Filed: Sep. 30, 1997

Related U.S. Application Data

[63] Continuation of application No. PCT/GB96/00757, Mar. 29, 1996.

[30] Foreign Application Priority Data

Mar. 31, 1995 [GB] United Kingdom .................... 9506684

[51] Int. Cl.$^7$ ........................... C12N 15/29; C12N 15/56; C12N 15/82; A01N 5/00
[52] U.S. Cl. .......................... 800/290; 800/278; 800/283; 800/286; 800/287; 800/298; 800/306; 435/200; 435/419; 435/468; 536/236; 536/24.1
[58] Field of Search .................................... 800/205, 283, 800/285, 306, 172.3, 278, 286, 287, 290, 298; 435/419, 200, 468; 536/23.6, 24.1

[56] References Cited

FOREIGN PATENT DOCUMENTS

| | | |
|---|---|---|
| 0 116 718 A1 | 8/1984 | European Pat. Off. . |
| 0 242 246 A1 | 10/1987 | European Pat. Off. . |
| 0 270 822 A1 | 6/1988 | European Pat. Off. . |
| 0 344 029 A1 | 11/1989 | European Pat. Off. . |
| 0 532 060 | 3/1993 | European Pat. Off. . |
| WO 92/11379 | 7/1992 | WIPO . |
| WO 94/01572 | 1/1994 | WIPO . |
| WO 94/23043 | 10/1994 | WIPO . |

OTHER PUBLICATIONS

Lewin, R. 1987. Science 237:1570.

Reeck et al. 1987. Cell 50:667.

Meakin et al. 1990. J. Exp. Bot. 41(229):1003–1011.

Kim et al. 1994. Plant Mol. Biol. 24:105–117.

Napoli et al. Introductionof a chimeric chalcone synthase gene into petunia results in reversible co–suppression of homologous genes in trans. The Plant cell. 2:279–289, Apr. 1990.

Smith et al. Antisense RNA inhibition of polygalacturonase gene expression in transgenic tomatoes. Nature. 334?724–726, Aug. 1988.

Petersen et al. An endo–polygalaturonase isoform potentially involved in pod dehiscence in oilseed rape. Plant Physiology 108(2 Suppl.):75, Annual Meeting Abstract No. 342, Jul.–Aug. 1995.

Altschul, S.F. et al., "Gapped BLAST and PSI–BLAST: a new generation of protein database search programs," *Nucl. Acids Res.* 25:3389–3402 (1997).

Coupe, S.A. et al., "Identification and characterization of a proline–rich mRNA that accumulates during pod development in oilseed rape (*Brassica napus* L.)," *Plant Mol. Biol.* 0:1–10 (1993).

Coupe, S.A. et al., "Characterization of a mRNA that accumulates during development of oilseed rape pods," *Plant Mol. Biol.* 0:1–5 (1993).

Coupe, S.A., "Changes in gene expression during pod development in oilseed rape (*Brassica napus* L.)," Thesis submitted to the University of Nottingham for the degree of Doctor of Philosophy (Oct. 1993).

Taylor, J.E. et al., "Changes in Polygalacturonase Activity and Solubility of Polyuronides during Ethylene–stimulated Leaf Abscission in *Sambucus nigra*," *J. Exp. Botany* 44:93–98 (Jan. 1993).

Webb, S.T.J. et al., "Purification of β1,4 glucanase from ethylene–treated leaflet abscission zones of *Sambucus nigra*," *Plant. Cell & Environ.* 16:329–333 (1993).

Bird, C.R., et al., "The tomato polygalacturonase gene and ripening–specific expression in transgenic plants," *Plant Molecular Biology* 11:651–662 (1988).

Bonghi, C., et al., "Cellulase and polygalacturonase involvement in the abscission of leaf and fruit explants of peach," *Plant Molecular Biology* 20:839–848 (1992).

Borkhardt, B., et al., "Changes in Cell Structure and Expression of Genes Encoding Polysaccharide Hydrolases During Pod Development in Oilseed Rape (*Brassica napus* L.)," *Pl. Physiol.* 105(1 Suppl.):56, Annual Meeting Abstract No. 261 (Jul.–Aug. 1994).

Christoffersen, R.E., and Laties, G.G., "Ethylene regulation of gene expression in carrots," *Proc. Natl. Acad. Sci. USA* 79:4060–4063 (1982).

Clarke, B.C., et al., "DNA analyses in wheat breeding," *Genome* 32:334–339 (1989).

Coupe, S.A., et al., "Identification and characterization of a proline–rich mRNA that accumulates during pod development in oilseed rape (*Brassica napus* L.)," *Plant Molecular Biology* 23:1223–1232 (1993).

Haseloff, J., and Gerlach, W.L., "Simple RNA enzymes with new and highly specific endoribonuclease activities," *Nature* 334:585–591 (1988).

Herrera–Estrella, L., et al., "Chimeric genes as dominant selectable markers in plant cells," *EMBO J.* 2(6):987–995 (1983).

(List continued on next page.)

*Primary Examiner*—David T. Fox
*Attorney, Agent, or Firm*—Sterne, Kessler, Goldstein & Fox P.L.L.C.

[57] ABSTRACT

The invention relates to the use of nucleic acid sequences coding for polygalacturonase in the control of dehiscence in plants. Plants transformed with such nucleic acid sequences are also disclosed.

43 Claims, 8 Drawing Sheets

OTHER PUBLICATIONS

Herrera–Estrella, L., et al., "Expression of chimaeric genes transferred into plant cells using a Ti–Plasmid–derived vector," *Nature* 303:209–213 (1983).

Jefferson, R.A., et al., "GUS fusions: β–glucuronidase a as sensitive and versatile gene fusion marker in higher plants," *EMBO J.* 6:3901–3907 (1987).

Jenkins, E.S., et al., "Characterization of an mRNA encoding a polygalaturonase expressed during pod development in oilseed rape (*Brassica napus* L.)," *Journal of Experimental Botany* 47(294):111–115 (Jan. 1996).

Meakin, P.J., and Roberts, J.A., "Dehiscene of Fruit in Oilseed Rape (*Brassica napus* L.). I. Anatomy of Pod Dehiscence," *Journal of Experimental Botany* 41(229):995–1002 (1990).

Meakin, P.J., and Roberts, J.A., "Dehiscence of Fruit in Oilseed Rape (*Brassica napus* L.). II. The Role of Cell Wall Degrading Enzymes and Ethylene," *Journal of Experimental Botany* 41(229):1003–1011 (1990).

Meakin, P.J., and Roberts, J.A., "Anatomical and Biochemical Changes Associated with the Induction of Oilseed Rape (*Brassica napus*) Pod Dehiscence by *Dasineura brassicae* (Winn.)," *Annals of Botany* 67:193–197 (1991).

Moloney, M.M., et al., "High efficiency transformation of *Brassica napus* using Agrobacterium vectors," *Plant Cell Reports* 8:238–242 (1989).

Petersen, M., et al., "An Endo–polygalacturonase Isoform Potentially Involved in Pod Dehiscence in Oilseed Rape," *Pl. Physiol.* 108(2 Suppl.):75, Annual Meeting Abstract No. 342 (Jul.–Aug. 1995).

Prakash, S., and Chopra, V.L., "Reconstruction of allpolyploid Brassicas through non–homologous recombination: introgression of resistance to pod shatter in *Brassica napus*," *Genet. Res., Camb.* 56(1):1–2 (1990).

Short, J.M., et al., "λ ZAP: a bacteriophage λ expression vector with in vivo excision properties," *Nucl. Acids Res.* 16:7583–7600 (1988).

Roberts, J.A., et al., "The Manipulation of Abscission in Agriculture," *Proceedings of the Symposium on the Physiology of Fruit Drop Ripening. Storage and Post Harvest Processing of Fruits*, 24–33 (1988).

```
GGCATCACGAGGGTACCCGTAAATCCCACCATACAACAAAGTTCTGTGAAAGTCTCCCAA  60

AAACTGCAAAGAGTCTCATATTAGTTCTTACTCTCAGAAATAAAACACACTCTTTCTGAA 120

AAGATTAGCGTTTCAAACCCCGAAATGGCCCGTTCTCATGGAAGTCTTGCTATTTTCTTA 180
                      M  A  R  C  H  G  S  L  A  I  F  L   12

TGCGTTCTTTTGATGCTCGCTTGCTGCCAAGCTTTGAGTAGCAACGTAGATGATGGATAT 240
 C  V  L  L  M  L  A  C  C  Q  A  L  S  S  N  V  D  D  G  Y   32

GGTCATGAAGATGGAAGCTTCGAAACCGATAGTTTAATCAAGCTCAACAACGACGACGAC 300
 G  H  E  D  G  S  F  E  T  D  S  L  I  K  L  N  N  D  D  D   52

GTTCTTACCTTGAAAAGCTCCGATAGACCCACTACCGAATCATCAACTGTTAGTGTTTCG 360
 V  L  T  L  K  S  S  D  R  P  T  T  E  S  S  T  V  S  V  S   72

AACTTCGGAGCAAAAGGTGATGGAAAAACCGATGATACTCAGGCTTTCAAGAAAGCATGG 420
 N  F  G  A  K  G  D  G  K  T  D  D  T  Q  A  F  K  K  A  W   92

AAGAAGGCATGTTCAACAAATGGAGTGACTACTTTCTTGATTCCTAAAGGGAAGACTTAT 480
 K  K  A  C  S  T  N  G  V  T  T  F  L  I  P  K  G  K  T  Y  112

CTCCTTAAGTCTATTAGATTCAGAGGCCCATGCAAATCATTACGTAGCTTCCAGATCCTA 540
 L  L  K  S  I  R  F  R  G  P  C  K  S  L  R  S  F  Q  I  L  132

GGCACTTTATCAGCTTCTACAAAACGATCGGATTACAGTAATGACAAGAACCACTGGCTT 600
 G  T  L  S  A  S  T  K  R  S  D  Y  S  N  D  K  N  H  W  L  152

ATTTTGGAGGACGTTAATAATCTATCAATCGATGGCGGCTCGGCGGGGATTGTTGATGGC 660
 I  L  E  D  V  N  N  L  S  I  D  G  G  S  A  G  I  V  D  G  172

AACGGAAAAATCTGGTGGCAAAACTCATGCAAAATCGACAAATCTAAGCCATGCACAAAA 720
 N  G  K  I  W  W  Q  N  S  C  K  I  D  K  S  K  P  C  T  K  192

GCGCCAACGGCTCTTACTCTCTACAACCTAAACAATTTGAATGTGAAGAATCTGAGAGTG 780
 A  P  T  A  L  T  L  Y  N  L  N  N  L  N  V  K  N  L  R  V  212

AGAAATGCACAGCAGATTCAGATTTCGATTGAGAAATGCAACAGTGTTGATGTTAAGAAT 840
 R  N  A  Q  Q  I  Q  I  S  I  E  K  C  N  S  V  D  V  K  N  232
```

FIG. 1A

```
GTTAAGATCACTGCTCCTGGCGATAGTCCCAACACGGATGGTATTCATATCGTTGCTACT    900
 V  K  I  T  A  P  G  D  S  P  N  T  D  G  I  H  I  V  A  T    252

AAAAACATTCGAATCTCCAATTCAGACATTGGGACAGGTGATGATTGCATATCCATTGAG    960
 K  N  I  R  I  S  N  S  D  I  G  T  G  D  D  C  I  S  I  E    272

GATGGATCGCAAAATGTTCAAATCAATGATTTAACTTGCGGCCCCGGTCATGGCATCAGC   1020
 D  G  S  Q  N  V  Q  I  N  D  L  T  C  G  P  G  H  G  I  S    292

ATTGGAAGCTTGGGGGATGACAATTCCAAAGCTTATGTATCGGGAATTAATGTGGATGGT   1080
 I  G  S  L  G  D  D  N  S  K  A  Y  V  S  G  I  N  V  D  G    312

GCTACGCTCTCTGAGACTGACAATGGAGTAAGAATCAAGACTTACCAGGGAGGGTCAGGA   1140
 A  T  L  S  E  T  D  N  G  V  R  I  K  T  Y  Q  G  G  S  G    332

ACTGCTAAGAACATTAAATTCCAAAACATTCGTATGGATAATGTCAAGAATCCGATCATA   1200
 T  A  K  N  I  K  F  Q  N  I  R  M  D  N  V  K  N  P  I  I    352

ATCGACCAGAACTACTGCGACAAGGACAAATGCGAACAACAAGAATCTGCGGTTCAAGTG   1260
 I  D  Q  N  Y  C  D  K  D  K  C  E  Q  Q  E  S  A  V  Q  V    372

AACAATGTCGTGTATCGGAACATACAAGGTACGAGCGCAACGGATGTGGCGATAATGTTT   1320
 N  N  V  V  Y  R  N  I  Q  G  T  S  A  T  D  V  A  I  M  F    392

AATTGCAGTGTGAAATATCCATGCCAAGGTATTGTGCTTGAGAATGTGAACATCAAAGGA   1380
 N  C  S  V  K  Y  P  C  Q  G  I  V  L  E  N  V  N  I  K  G    412

GGAAAAGCTTCTTGCAAAAATGTCAATGTTAAGGATAAAGGCACCGTTTCTCCTAAATGC   1440
 G  K  A  S  C  K  N  V  N  V  K  D  K  G  T  V  S  P  K  C    432

CCTTAATTACTAAGTTGATTATGTAATATACATAAATACGTATTATATGTGGTTATAGAT   1500
 P                                                              433

GCCATCTATATCCTTATCTACGTATTGATTCTCGATATATATAGAAAACTAAGGATTTAT   1560

GGGAATATACATACAATAGTTGAGATAATTGTTGTCTTGTATATGGTTCACTGAAGTTGA   1620

TTGCTTGTCCACGAATAAATGAATAATGTCATTTGTC                          1657
```

FIG. 1B

TGGCGAATTCCGAATACGGACGGTATTCATATCGTTGCTACTAAA 45
         P  N  T  D  G  I  H  I  V  A  T  K  12

AACATTCGAATCTCCAATTCAGACATTGGGACAGGTGATGATTGC 90
 N  I  R  I  S  N  S  D  I  G  T  G  D  D  C  27

ATATCCATTGAGGATGGATCGCAAAATGTTCAAATCAATGATTTA 135
 I  S  I  E  D  G  S  Q  N  V  Q  I  N  D  L  42

ACTTGCGGCCCCGGTCACGGCCTAGGTGG              164
 T  C  G  P  G  H  G                        49

NON-Z

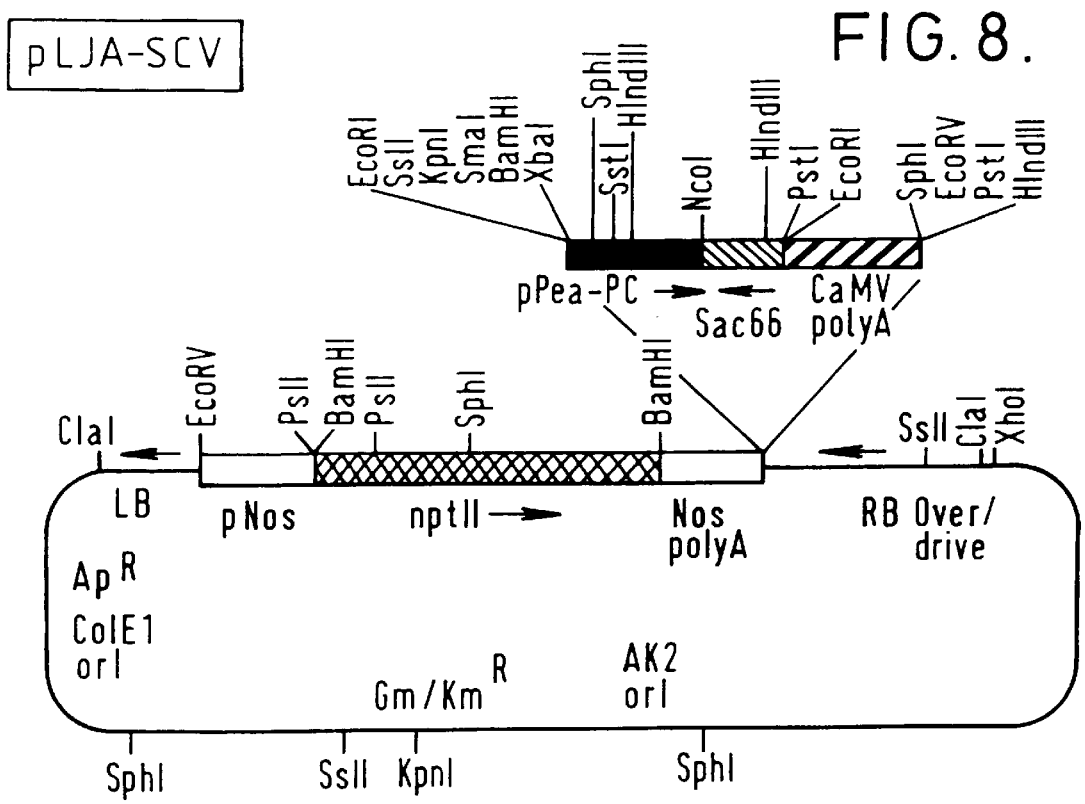
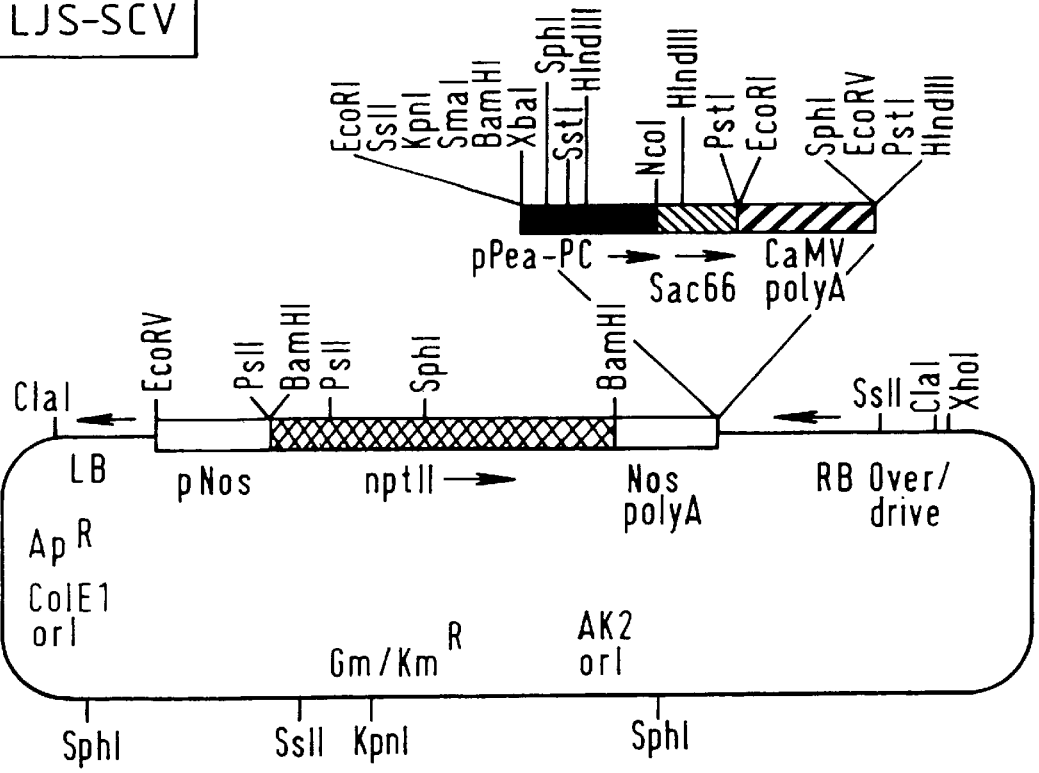
FIG. 8.

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 1:

Pro Asn Thr Asp Gly
   1               5

(2) INFORMATION FOR SEQ ID NO: 2:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 2:

Cys Gly Pro Gly His Gly
   1               5

(2) INFORMATION FOR SEQ ID NO: 3:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 3:

Gly Pro Gly His Gly
   1               5

(2) INFORMATION FOR SEQ ID NO: 4:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 4:

GAGAGAGGAT CCTCGAGTTT TTTTTTTTTT TTTT                                    34

(2) INFORMATION FOR SEQ ID NO: 5:

(i) SEQUENCE CHARACTERISTICS:
       (A) LENGTH: 1657 base pairs
       (B) TYPE: nucleic acid
       (C) STRANDEDNESS: single
       (D) TOPOLOGY: linear

```
    (ii) MOLECULE TYPE: cDNA (ix) FEATURE:
         (A) NAME/KEY: CDS
         (B) LOCATION:145..1446

(xi) SEQUENCE DESCRIPTION: SEQ ID NO: 5:

GGCATCACGA GGGTACCCGT AAATCCCACC ATACAACAAA GTTCTGTGAA AGTCTCCCAA       60

AAACTGCAAA GAGTCTCATA TTAGTTCTTA CTCTCAGAAA TAAAACACAC TCTTTCTGAA      120

AAGATTAGCG TTTCAAACCC CGAA ATG GCC CGT TGT CAT GGA AGT CTT GCT        171
                          Met Ala Arg Cys His Gly Ser Leu Ala
                            1               5

ATT TTC TTA TGC GTT CTT TTG ATG CTC GCT TGC TGC CAA GCT TTG AGT        219
Ile Phe Leu Cys Val Leu Leu Met Leu Ala Cys Cys Gln Ala Leu Ser
 10              15                  20                  25

AGC AAC GTA GAT GAT GGA TAT GGT CAT GAA GAT GGA AGC TTC GAA ACC        267
Ser Asn Val Asp Asp Gly Tyr Gly His Glu Asp Gly Ser Phe Glu Thr
                 30                  35                  40

GAT AGT TTA ATC AAG CTC AAC AAC GAC GAC GAC GTT CTT ACC TTG AAA        315
Asp Ser Leu Ile Lys Leu Asn Asn Asp Asp Asp Val Leu Thr Leu Lys
             45                  50                  55

AGC TCC GAT AGA CCC ACT ACC GAA TCA TCA ACT GTT AGT GTT TCG AAC        363
Ser Ser Asp Arg Pro Thr Thr Glu Ser Ser Thr Val Ser Val Ser Asn
         60                  65                  70

TTC GGA GCA AAA GGT GAT GGA AAA ACC GAT GAT ACT CAG GCT TTC AAG        411
Phe Gly Ala Lys Gly Asp Gly Lys Thr Asp Asp Thr Gln Ala Phe Lys
     75                  80                  85

AAA GCA TGG AAG AAG GCA TGT TCA ACA AAT GGA GTG ACT ACT TTC TTG        459
Lys Ala Trp Lys Lys Ala Cys Ser Thr Asn Gly Val Thr Thr Phe Leu
 90                  95                 100                 105

ATT CCT AAA GGG AAG ACT TAT CTC CTT AAG TCT ATT AGA TTC AGA GGC        507
Ile Pro Lys Gly Lys Thr Tyr Leu Leu Lys Ser Ile Arg Phe Arg Gly
                110                 115                 120

CCA TGC AAA TCA TTA CGT AGC TTC CAG ATC CTA GGC ACT TTA TCA GCT        555
Pro Cys Lys Ser Leu Arg Ser Phe Gln Ile Leu Gly Thr Leu Ser Ala
            125                 130                 135

TCT ACA AAA CGA TCG GAT TAC AGT AAT GAC AAG AAC CAC TGG CTT ATT        603
Ser Thr Lys Arg Ser Asp Tyr Ser Asn Asp Lys Asn His Trp Leu Ile
        140                 145                 150

TTG GAG GAC GTT AAT AAT CTA TCA ATC GAT GGC GGC TCG GCG GGG ATT        651
Leu Glu Asp Val Asn Asn Leu Ser Ile Asp Gly Gly Ser Ala Gly Ile
    155                 160                 165

GTT GAT GGC AAC GGA AAA ATC TGG TGG CAA AAC TCA TGC AAA ATC GAC        699
Val Asp Gly Asn Gly Lys Ile Trp Trp Gln Asn Ser Cys Lys Ile Asp
170                 175                 180                 185

AAA TCT AAG CCA TGC ACA AAA GCG CCA ACG GCT CTT ACT CTC TAC AAC        747
Lys Ser Lys Pro Cys Thr Lys Ala Pro Thr Ala Leu Thr Leu Tyr Asn
                190                 195                 200

CTA AAC AAT TTG AAT GTG AAG AAT CTG AGA GTG AGA AAT GCA CAG CAG        795
Leu Asn Asn Leu Asn Val Lys Asn Leu Arg Val Arg Asn Ala Gln Gln
            205                 210                 215

ATT CAG ATT TCG ATT GAG AAA TGC AAC AGT GTT GAT GTT AAG AAT GTT        843
Ile Gln Ile Ser Ile Glu Lys Cys Asn Ser Val Asp Val Lys Asn Val
        220                 225                 230

AAG ATC ACT GCT CCT GGC GAT AGT CCC AAC ACG GAT GGT ATT CAT ATC        891
Lys Ile Thr Ala Pro Gly Asp Ser Pro Asn Thr Asp Gly Ile His Ile
    235                 240                 245

GTT GCT ACT AAA AAC ATT CGA ATC TCC AAT TCA GAC ATT GGG ACA GGT        939
Val Ala Thr Lys Asn Ile Arg Ile Ser Asn Ser Asp Ile Gly Thr Gly
250                 255                 260                 265
```

```
GAT GAT TGC ATA TCC ATT GAG GAT GGA TCG CAA AAT GTT CAA ATC AAT        987
Asp Asp Cys Ile Ser Ile Glu Asp Gly Ser Gln Asn Val Gln Ile Asn
                270                 275                 280

GAT TTA ACT TGC GGC CCC GGT CAT GGC ATC AGC ATT GGA AGC TTG GGG       1035
Asp Leu Thr Cys Gly Pro Gly His Gly Ile Ser Ile Gly Ser Leu Gly
            285                 290                 295

GAT GAC AAT TCC AAA GCT TAT GTA TCG GGA ATT AAT GTG GAT GGT GCT       1083
Asp Asp Asn Ser Lys Ala Tyr Val Ser Gly Ile Asn Val Asp Gly Ala
        300                 305                 310

ACG CTC TCT GAG ACT GAC AAT GGA GTA AGA ATC AAG ACT TAC CAG GGA       1131
Thr Leu Ser Glu Thr Asp Asn Gly Val Arg Ile Lys Thr Tyr Gln Gly
    315                 320                 325

GGG TCA GGA ACT GCT AAG AAC ATT AAA TTC CAA AAC ATT CGT ATG GAT       1179
Gly Ser Gly Thr Ala Lys Asn Ile Lys Phe Gln Asn Ile Arg Met Asp
330                 335                 340                 345

AAT GTC AAG AAT CCG ATC ATA ATC GAC CAG AAC TAC TGC GAC AAG GAC       1227
Asn Val Lys Asn Pro Ile Ile Ile Asp Gln Asn Tyr Cys Asp Lys Asp
                350                 355                 360

AAA TGC GAA CAA CAA GAA TCT GCG GTT CAA GTG AAC AAT GTC GTG TAT       1275
Lys Cys Glu Gln Gln Glu Ser Ala Val Gln Val Asn Asn Val Val Tyr
            365                 370                 375

CGG AAC ATA CAA GGT ACG AGC GCA ACG GAT GTG GCG ATA ATG TTT AAT       1323
Arg Asn Ile Gln Gly Thr Ser Ala Thr Asp Val Ala Ile Met Phe Asn
        380                 385                 390

TGC AGT GTG AAA TAT CCA TGC CAA GGT ATT GTG CTT GAG AAT GTG AAC       1371
Cys Ser Val Lys Tyr Pro Cys Gln Gly Ile Val Leu Glu Asn Val Asn
    395                 400                 405

ATC AAA GGA GGA AAA GCT TCT TGC AAA AAT GTC AAT GTT AAG GAT AAA       1419
Ile Lys Gly Gly Lys Ala Ser Cys Lys Asn Val Asn Val Lys Asp Lys
410                 415                 420                 425

GGC ACC GTT TCT CCT AAA TGC CCT TAA TTACTAAGTT GATTATGTAA             1466
Gly Thr Val Ser Pro Lys Cys Pro *
                430

TATACATAAA TACGTATTAT ATGTGGTTAT AGATGCCATC TATATCCTTA TCTACGTATT     1526

GATTCTCGAT ATATATAGAA AACTAAGGAT TTATGGGAAT ATACATACAA TAGTTGAGAT     1586

AATTGTTGTC TTGTATATGG TTCACTGAAG TTGATTGCTT GTCCACGAAT AAATGAATAA     1646

TGTCATTTGT C                                                          1657

(2) INFORMATION FOR SEQ ID NO: 6:

(i) SEQUENCE CHARACTERISTICS:
        (A) LENGTH: 433 amino acids
        (B) TYPE: amino acid
        (D) TOPOLOGY: linear (ii) MOLECULE TYPE: protein (xi) SEQUENCE DESCRIPTION: SEQ ID NO: 6:

Met Ala Arg Cys His Gly Ser Leu Ala Ile Phe Leu Cys Val Leu Leu
 1               5                  10                  15

Met Leu Ala Cys Cys Gln Ala Leu Ser Ser Asn Val Asp Asp Gly Tyr
            20                  25                  30

Gly His Glu Asp Gly Ser Phe Glu Thr Asp Ser Leu Ile Lys Leu Asn
        35                  40                  45

Asn Asp Asp Asp Val Leu Thr Leu Lys Ser Ser Asp Arg Pro Thr Thr
    50                  55                  60

Glu Ser Ser Thr Val Ser Val Ser Asn Phe Gly Ala Lys Gly Asp Gly
65                  70                  75                  80
```

```
Lys Thr Asp Asp Thr Gln Ala Phe Lys Lys Ala Trp Lys Lys Ala Cys
                    85                  90                  95

Ser Thr Asn Gly Val Thr Thr Phe Leu Ile Pro Lys Gly Lys Thr Tyr
            100                 105                 110

Leu Leu Lys Ser Ile Arg Phe Arg Gly Pro Cys Lys Ser Leu Arg Ser
        115                 120                 125

Phe Gln Ile Leu Gly Thr Leu Ser Ala Ser Thr Lys Arg Ser Asp Tyr
    130                 135                 140

Ser Asn Asp Lys Asn His Trp Leu Ile Leu Glu Asp Val Asn Asn Leu
145                 150                 155                 160

Ser Ile Asp Gly Gly Ser Ala Gly Ile Val Asp Gly Asn Gly Lys Ile
                165                 170                 175

Trp Trp Gln Asn Ser Cys Lys Ile Asp Lys Ser Lys Pro Cys Thr Lys
            180                 185                 190

Ala Pro Thr Ala Leu Thr Leu Tyr Asn Leu Asn Asn Leu Asn Val Lys
        195                 200                 205

Asn Leu Arg Val Arg Asn Ala Gln Gln Ile Gln Ile Ser Ile Glu Lys
    210                 215                 220

Cys Asn Ser Val Asp Val Lys Asn Val Lys Ile Thr Ala Pro Gly Asp
225                 230                 235                 240

Ser Pro Asn Thr Asp Gly Ile His Ile Val Ala Thr Lys Asn Ile Arg
                245                 250                 255

Ile Ser Asn Ser Asp Ile Gly Thr Gly Asp Asp Cys Ile Ser Ile Glu
            260                 265                 270

Asp Gly Ser Gln Asn Val Gln Ile Asn Asp Leu Thr Cys Gly Pro Gly
        275                 280                 285

His Gly Ile Ser Ile Gly Ser Leu Gly Asp Asp Asn Ser Lys Ala Tyr
    290                 295                 300

Val Ser Gly Ile Asn Val Asp Gly Ala Thr Leu Ser Glu Thr Asp Asn
305                 310                 315                 320

Gly Val Arg Ile Lys Thr Tyr Gln Gly Gly Ser Gly Thr Ala Lys Asn
                325                 330                 335

Ile Lys Phe Gln Asn Ile Arg Met Asp Asn Val Lys Asn Pro Ile Ile
            340                 345                 350

Ile Asp Gln Asn Tyr Cys Asp Lys Asp Lys Cys Glu Gln Gln Glu Ser
        355                 360                 365

Ala Val Gln Val Asn Asn Val Val Tyr Arg Asn Ile Gln Gly Thr Ser
    370                 375                 380

Ala Thr Asp Val Ala Ile Met Phe Asn Cys Ser Val Lys Tyr Pro Cys
385                 390                 395                 400

Gln Gly Ile Val Leu Glu Asn Val Asn Ile Lys Gly Gly Lys Ala Ser
                405                 410                 415

Cys Lys Asn Val Asn Val Lys Asp Lys Gly Thr Val Ser Pro Lys Cys
            420                 425                 430

Pro (2) INFORMATION FOR SEQ ID NO: 7:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (ii) MOLECULE TYPE: cDNA
```

```
        (ix) FEATURE:
              (A) NAME/KEY: CDS
              (B) LOCATION:10..156

(xi) SEQUENCE DESCRIPTION: SEQ ID NO: 7:

TGGCGAATT CCG AAT ACG GAC GGT ATT CAT ATC GTT GCT ACT AAA AAC              48
          Pro Asn Thr Asp Gly Ile His Ile Val Ala Thr Lys Asn
          435                 440                 445

ATT CGA ATC TCC AAT TCA GAC ATT GGG ACA GGT GAT GAT TGC ATA TCC           96
Ile Arg Ile Ser Asn Ser Asp Ile Gly Thr Gly Asp Asp Cys Ile Ser
        450                 455                 460

ATT GAG GAT GGA TCG CAA AAT GTT CAA ATC AAT GAT TTA ACT TGC GGC          144
Ile Glu Asp Gly Ser Gln Asn Val Gln Ile Asn Asp Leu Thr Cys Gly
        465                 470                 475

CCC GGT CAC GGC CTAGGTGG                                                 164
Pro Gly His Gly
480

(2) INFORMATION FOR SEQ ID NO: 8:

(i) SEQUENCE CHARACTERISTICS:
              (A) LENGTH: 49 amino acids
              (B) TYPE: amino acid
              (D) TOPOLOGY: linear (ii) MOLECULE TYPE: protein (xi) SEQUENCE DESCRIPTION: SEQ ID NO: 8:

Pro Asn Thr Asp Gly Ile His Ile Val Ala Thr Lys Asn Ile Arg Ile
1               5                   10                  15

Ser Asn Ser Asp Ile Gly Thr Gly Asp Asp Cys Ile Ser Ile Glu Asp
            20                  25                  30

Gly Ser Gln Asn Val Gln Ile Asn Asp Leu Thr Cys Gly Pro Gly His
        35                  40                  45

Gly
```

CONTROL OF POD DEHISCENCE

This application is a continuation of PCT/GB96/00757 filed Mar. 29, 1996.

FIELD OF THE INVENTION

This invention relates generally to the control of pod dehiscence or shatter.

BACKGROUND OF THE INVENTION

Abscission is the process that causes the shedding of a range of plant parts, including leaves, flowers and fruit. The process occurs at precise sites and involves coordinated cell wall breakdown. Associated with cell separation is an increase in the activity of several hydrolytic enzymes including β-1,4-glucanase (cellulase, EC 3.1.2.4) and polygalacturonase (PG EC 3.2.1.15).

The process of pod dehiscence, or shatter as it is commonly termed, in oilseed rape (*Brassica napus*) and other crops shares a number of features with abscission. Degradation and separation of cell walls occurs along a discrete layer of cells, termed the dehiscence zone, and a localised increase in the activity of cellulase has been reported prior to the onset of dehiscence (Meakin and Roberts *J. Exp. Bot.* 41(229) 995–1002 (1990) and *J. Exp. Bot.* 41(229) 1003–1011 (1990)). This process is agronomically important because it may result in the premature shedding of seed before the crop can be harvested. Adverse weather conditions can exacerbate the process resulting in a greater than 50% loss of seed. This loss of seed not only has a dramatic effect on yield but also results in the emergence of the crop as a weed in the subsequent growing season.

Attempts to solve this problem over the last 20 years have focused on the breeding of shatter-resistant varieties. The most commonly used method is by trying to introduce germplasm from related species by interspecific hybridisation. Related species such as *B. nigra, B. juncea* and *B. campestris* have been used for this purpose but resulting plants from these crosses are frequently sterile and lose favourable characteristics which have to be regained by back crossing. This is both time consuming and laborious. The interspecific hybridisation strategy also has to cope with transferring two or more genes which are recessive in action into each of the breeding lines. Indeed, even within *B. campestris*, different genetic backgrounds have revealed different numbers of genes to be important in shatter resistance. This has necessitated breeders performing test crosses at each generation during the attempt to produce elite material. These difficulties have been compounded by the fact that shattering is a difficult and time-consuming trait to assess in the field. All these factors may account for the fact that the conventional breeding approach has made no progress over the last twenty years.

Other methods employed to try and alleviate the problem include chemicals, in the form of desiccants and pod sealants. The most widely used method to try and prevent seed loss is the mechanical technique of swathing in order to get uniform desiccation of the crop and reduce shattering by wind which occurs in the upright crop.

This invention takes a completely different approach to solve the problem of dehiscence: it involves the use of recombinant DNA technology. In 1988, when plant biotechnology had reached an age of some considerable sophistication, Roberts and Taylor speculated:

By regulating cell separation at abscission sites, it may be possible . . . to also influence related processes such as pod dehiscence. (*Proceedings of the Symposium on the Physiology of Fruit Drop, Ripening, Storage and Post-Harvest Processing of Fruits*, Turin, 3–4 October 1988, pp 24–33).

However, without any indication of which genes may be involved in such processes, this exhortation did little to enable the art to address the problem at the cell or genetic level.

WO94/23043 discloses nucleic acid sequences encoding proteins involved in plant abscission or dehiscence. However this disclosure does not include any discussion of polygalacturonase's role in abscission or dehiscence.

Meakin and Roberts (supra) reported that there was no correlation between the timing of dehiscence and the activity of the pectin degrading enzyme, polygalacturonase (PG). Although they stated that it was not possible to discount a role for PG in pod shatter, their work did not provide any evidence that activity of the enzyme was related to timing of dehiscence.

SUMMARY OF THE INVENTION

It has now been discovered that, in fact, PG is implicated in dehiscence and that manipulation of this enzyme's activity can influence the timing of dehiscence. The gene coding for PG has a pattern of expression which is, spatially and/or temporally, specific or at least preferential for tissue involved in dehiscence. The invention relates to the exploitation of the gene and related DNA sequences (including regulatory sequences) in the manipulation of pod dehiscence including its reduction or prevention in particular.

DESCRIPTION OF THE PREFERRED EMBODIMENTS

According to a first aspect of the present invention, there is provided the use of a recombinant or isolated nucleic acid sequence which encodes the enzyme polygalacturonase in the control of dehiscence.

The invention has application to, all crops which have a dehiscence zone and may therefore lose seed pre-harvest because of cell separation events. An economically important plant genus to which the invention can be applied is that of Brassica, eg the important crop *Brassica napus*.

In particular, the polygalacturonase will be preferentially or specifically expressed in the dehiscence zone of pericarp tissue. In one embodiment, the pericarp tissue is from the genus Brassica, preferably *Brassica napus*. Suitably, the nucleic acid sequence will be a DNA sequence.

Recombinant or isolated nucleic acid sequences which can be used in this invention are illustrated by the nucleic acid sequence of FIGS. 1A and 1B (SEQ ID NO:5), which encodes the amino acid sequence shown in FIGS. 1A and 1B (SEQ ID NO: 6). All other nucleic acid sequences which, by virtue of the degeneracy of the genetic code, also code for the given amino acid sequence are also useful for the practice of the present invention. Nucleic acid sequences which are substantially homologous to nucleic acid sequences encoding the amino acid sequence shown in FIGS. 1A and 1B (SEQ ID NO:6) can also be employed.

"Substantial homology" may be assessed either at the nucleic acid level or at the amino acid level. At the nucleic acid level, sequences having substantial homology may be regarded as those which hybridise to the nucleic acid sequences shown in FIGS. 1A and 1B (SEQ ID NO:5) under stringent conditions (for example at 35 to 65° C. in a salt solution of about 0.9 M). At the amino acid level, a protein sequence may be regarded as substantially homologous to another protein sequence if a significant number of the constituent amino acids exhibit homology. At least 40%, 50%, 60%, 70%, 80%, 90%, 95% or even 99%, in increasing order of preference, of the amino acids may be homologous.

The skilled man will also appreciate that modified proteins may also be employed. "Protein engineering" techniques are now well established in the art and it is within the scope of the present invention to utilise polygalacturonase enzymes which have been so "engineered" to modify their properties. For instance, their specificity or kinetics may be altered in some way in order to be more effective. The essential feature which they must retain of course is activity as a polygalacturonase enzyme.

Preferably, the nucleic acid used in the invention will include a promoter or other regulatory sequence which naturally controls expression of polygalacturonase. Since it has been found that PG is expressed during dehiscence, such promoters are themselves useful in controlling this process. The skilled man will appreciate that it may not be necessary to utilise the whole promoter. Only essential regulatory elements may be used and in fact such elements can be used to construct chimeric sequences or promoters. The essential requirement is of course to retain the tissue and/or temporal specificity.

In a second aspect, the invention provides the use of the enzyme polygalacturonase in the control of dehiscence.

As described above the promoters or other regulatory sequences (including synthetic or chimeric promoters) which are capable of driving expression of polygalacturonase in the dehiscence zone are also useful in controlling dehiscence. Thus, in a third aspect, the present invention provides a nucleic acid sequence which is a promoter or other regulatory sequence which naturally controls expression of polygalacturonase.

In a fourth aspect, the present invention provides the use of such promoters or other regulatory sequences in the control of dehiscence.

While promoters as described above may drive DNA encoding an enzyme, they may alternatively drive DNA whose transcription product is itself deleterious. Examples of such transcription products include sense constructs (which may act by co-suppression), antisense RNA and ribozymes.

As far as antisense nucleic acid is concerned, introducing the coding region of a gene in the reverse orientation to that found in nature can result in the down-regulation of the gene and hence the production of less or none of the gene product. The RNA transcribed from antisense DNA is capable of binding to, and destroying the function of, a sense RNA of the sequence normally found in the cell, thereby disrupting function. Examples of suitable antisense DNAs are the antisense DNAs of the sequence shown in FIGS. 1A and 1B (SEQ ID NO:5). Since this sequence is normally expressed in the dehiscence zone, antisense sequences to it may be expected to disrupt normal dehiscence.

Ribozymes are RNA "enzymes" capable of highly specific cleavage against a given target sequence (Haseloff and Gerlach, Nature 334 585–591 (1988)).

Promoters useful as described above may be located in cDNA or genomic libraries using, for example, probe sequences taken from the nucleic acid sequence of FIGS. 1A and 1B (SEQ ID NO:5).

Nucleic acid useful in the invention includes that which, when introduced into a plant, prevents or otherwise interferes with normal dehiscence by interfering with the normal expression of polygalacturonase. Of course, dehiscence-specific promoters, as discussed above, may be useful in this feature of the invention. However, there is a broader dimension which must be considered: antisense DNA or ribozyme-encoding DNA specific for polygalacturonase need not be driven by dehiscence-specific promoters. Instead, they could be driven by constitutive or other promoters (such as for example the CaMV 35S, rubisco or plastocyanin promoter). If the sense gene is only expressed in the pod, there will with an antisense approach be no pleiotropic effects on plant development, and only the development of the dehiscence zone will be disrupted. A ribozyme gene expressed throughout the plant will not result in a translated protein product, and so may require less metabolic energy than the synthesis of a gene product throughout most of the plant.

Antisense technology and ribozyme technologies have already found application in other areas of plant molecular biology. For example, antisense technology has been used to control tomato fruit ripening. Ribozyme technology has been used to control viral infection of melons.

While DNA or RNA in accordance with this feature of the invention generally interferes with the proper expression of polygalacturonase genes during pod development, in preferred embodiments expression is substantially prevented.

In preferred embodiments of the invention, 3'-transcription regulation signals, including a polyadenylation signal, may be provided as part of the nucleic acid sequences. Preferred 3'-transcription regulation signals may be derived from the cauliflower mosaic virus 35S gene. It should be recognised that other 3'-transcription regulation signals could also be used.

The nucleic acid used in the invention may be in the form of a vector. The vector may for example be a plasmid, cosmid or phage. Vectors will frequently include one or more selectable markers to enable selection of cells transfected (or transformed: the terms are used interchangeably in this specification) with them and, preferably, to enable selection of cells harbouring vectors incorporating heterologous DNA. Appropriate start and stop signals will generally be present. Additionally, if the vector is intended for expression, sufficient regulatory sequences to drive expression will be present; however, nucleic acid for use in the invention will generally be expressed in plant cells, and so microbial host expression would not be among the primary objectives of the invention, although it is not ruled out. Vectors not including regulatory sequences are useful as cloning vectors.

Cloning vectors can be introduced into E. coli or another suitable host which facilitate their manipulation. According to another aspect of the invention, there is therefore provided a host cell transfected or transformed with nucleic acid as described above.

Nucleic acid for use in the invention can be prepared by any convenient method involving coupling together successive nucleotides, and/or ligating oligo- and/or polynucleotides, including in vitro processes, but recombinant DNA technology forms the method of choice.

Ultimately, nucleic acid for use in the invention will where appropriate be introduced into plant cells, by any suitable means.

Preferably, nucleic acid is transformed into plant cells using a disarmed Ti-plasmid vector and carried by Agrobacterium by procedures known in the art, for example as described in EP-A-0116718 and EP-A-0270822. Alternatively, the foreign nucleic acid could be introduced directly into plant cells using an electrical discharge apparatus. This method is preferred where Agrobacterium is ineffective, for example where the recipient plant is monocotyledonous. Any other method that provides for the stable incorporation of the nucleic acid within the nuclear DNA of any plant cell of any species would also be suitable. This includes species of plant which are not currently capable of genetic transformation.

Preferably nucleic acid for use in the invention also contains a second chimeric gene (a "marker" gene) that enables a transformed plant containing the foreign nucleic acid to be easily distinguished from other plants that do not contain the foreign nucleic acid. Examples of such a marker gene include antibiotic resistance (Herrera-Estrella et al., *EMBO J.* 2(6) 987–95 (1983) and Herrera-Estrella et al., *Nature* 303 209–13 (1983)), herbicide resistance (EP-A-0242246) and glucuronidase (GUS) expression (EP-A-0344029). Expression of the marker gene is preferably controlled by a second promoter which allows expression in cells other than the tapetum, thus allowing selection of cells or tissue containing the marker at any stage of regeneration of the plant. The preferred second promoter is derived from the gene which encodes the 35S subunit of Cauliflower Mosaic Virus (CaMV) coat protein. However any other suitable second promoter could be used.

A whole plant can be regenerated from a single transformed plant cell, and the invention therefore provides transgenic plants (or parts of them, such as propagating material) including nucleic acid as defined herein. The regeneration can proceed by known methods.

Thus, in further aspects, the present invention provides:

(i) a transgenic plant which includes a nucleic acid sequence as defined herein;

(ii) an oilseed rape plant which is shatter resistant;

(iii) a plant cell which includes a nucleic acid sequence as defined herein;

(iv) propagating material derived from transgenic plants of the invention;

(v) seeds derived from transgenic plants of the invention; and (vi) a method of regulating dehiscence, which comprises the step of transforming or transfecting propagating material from a plant with a nucleic acid sequence as defined herein.

Preferred features of each aspect of the invention are as for each other aspect mutatis mutandis.

BRIEF DESCRIPTION OF THE DRAWINGS

The invention will now be illustrated by the following Examples. The Examples refer to the accompanying drawings, in which:

FIGS. 1A and 1B: show the nucleic acid (SEQ ID NO:5) and corresponding amino acid (SEQ ID NO:6) sequence of SAC66;

FIG. 2: shows the sequence of the 164 bp PCR fragment of SAC66 (SEQ ID NO:7 and 8);

FIG. 8: shows the construction of expression cassettes as described in example 5.

EXAMPLES

Example 1

Cloning of pSAC66

Plant Material

Figure 3:
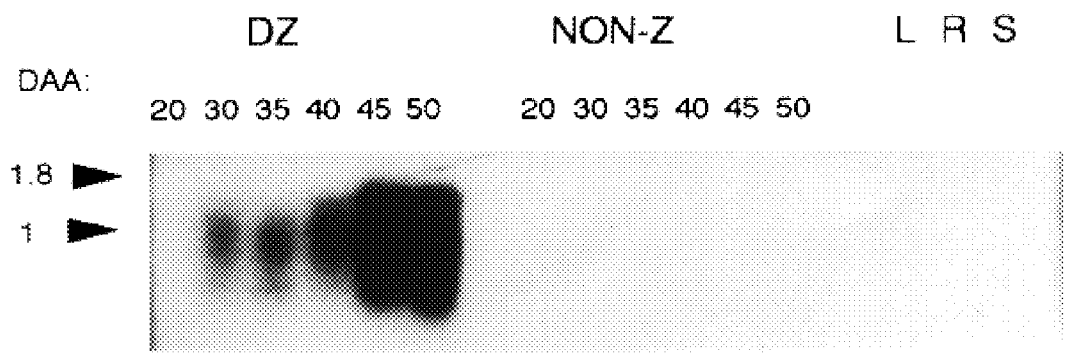
FIG. 3: shows the northern blot analysis of SAC66.

Seeds of *B. napus* cv Rafal were grown as described by Meakin and Roberts, (*J. Exp. Bot.* 41(229) 995–1002 (1990)) with the following modifications. Single seedlings were potted into 10 cm pots containing Levington M2 compost, and after vernalisation for 6 weeks, were re-potted into 21 cm pots. Infection by powdery mildew or aphids was controlled by the application of Safers fungicide. At anthesis, tags were applied daily to record flower opening. This procedure facilitated accurate age determination of each pod. Pods were harvested at various days after anthesis (DAA). The dehiscence zone was excised from the non-zone material and seed using a scalpel blade using the method of Meakin and Roberts (*J. Exp. Bot.* 41: 1003–1011 (1990)) and immediately frozen in liquid $N_2$ prior to storage at −70° C.

RNA Isolation

All chemicals were molecular biology grade and bought from either Sigma Chemical Ltd (Dorset, UK), or ICN Biomedicals. Total RNA was extracted using the polysomal extraction method of Christoffersen and Laties, *Proc. Natl. Acad. Sci.* 79 4060–4063 (1982), with the following alterations. The plant material was ground to a powder in liquid $N_2$ and then in 10 volumes of extraction buffer (200 mM Tris-acetate [pH 8.2], 100 mM magnesium acetate, 20 mM potassium acetate, 20 mM EDTA, 5% w/v sucrose, after sterilisation 2-mercaptoethanol was added to 15 mM and cycloheximide added to a final concentration of 0.1 mg ml$^{-1}$). The supernatant was then layered over 8 ml 1 M sucrose made with extraction buffer and centrifuged in a KONTRON (Switzerland) TFT 70.38 rotor at 45,000 rpm (150,000 g) for 2 hr at 2° C. in a Kontron CENTRIKON T-1065 ultra-centrifuge. Pellets were then resuspended in 500 μl 0.1 M sodium acetate, 0.1% SDS, pH 6.0 and phenol/chloroform (1:1 v/v) extracted and the total RNA precipitated. mRNA was isolated from the total population of nucleic acids extracted from the dehiscence zone and non-zone tissue at 40, 45 and 50 DAA pods, using the Poly(A) quick mRNA purification kit (Stratagene, Cambridge UK), and was used to make 1st strand cDNA using reverse transcriptase.

PCR with degenerate primers

Degenerate primers were designed by multiple sequence alignments of known fruit-specific and pollen-specific polygalacturonase (PG) mRNA sequences. Two primers were synthesized in the 5' to 3' direction (P1 and P2) to prime with a polyT primer (OG2) and one in the 3' to 5' direction (P3) for a nested PCR approach with P1.

Sequences of each primer and the relative positions of P1, P2 and P3 on a PG mRNA sequence are shown below.

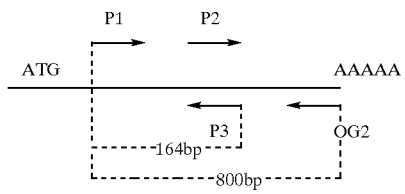

Degenerate primers were designed on PG consensus amino acids. Restriction enzyme sites were included in each primer.

P1: (EcoRI) PNTDG (SEQ ID NO:1)
P2: (EcoRI) CGPGHG (SEQ ID NO:2)
P3: GPGHG (BamHI) (SEQ ID NO:3)
OG2: 5' GAGAGAGGATCCTCGAG ... T(×17) 3' (SEQ ID NO:4)

Each PCR reaction contained 1×PCR buffer, 1.5 U Taq polymerase, 2 µg degenerate primer, 200 ng non-degenerate primer and 2 ng first strand cDNA in a total volume of 20 µl was overlaid with 18 µl mineral oil. PCR buffer (1×) contained 45 mM tris-HCl pH 8.8, 11 mM ammonium sulphate, 4.5 mM magnesium chloride, β-mercaptoethanol, 4.5 mM EDTA pH8, 10 mM of each dNTP and 0.1 mg ml BSA.

PCR cycles were as follows: 20 PCR cycles included a denaturation temperature of 94° C. for 1 min, primer annealing temperature of 45° C. for 2 min and extension temperature of 72° C. for 2 min. During the following 5 cycles, the Taq polymerase extension time was increased to 2.5 min and in the final cycles for 3 min. The reactions were carried out on a Techne Thermocycler model PHC-3 using a ramp rate of 1° C./sec.

A sample of the PCR reaction (10 µl) was run on a 2% agarose gel and DNA of the predicted size eluted using either a "gelase" kit (nbl gene sciences Northumberland UK) for products less than 500 bp or a "geneclean" kit (Bio. c/o Statech, Cambs, UK) for products greater than 500 bp. The final pellet was resuspended in 20 µl, and 2 µl were used in subsequent PCR reactions.

cDNA Library Screening

Three plates each containing approximately 40,000 recombinant plaques from a dehiscence-related cDNA library generated by Coupe et al, *Plant Mol. Biol.* (1993), were screened with a radio-labelled 164 bp (shown in FIG. 2) fragment derived from the nested PCR approach described above using in situ plaque hybridisation. Duplicate plaque lifts were obtained using HYBOND™ N+ membranes (Amersham, Aylesbury, UK) and were then treated and hybridised according to manufacturers' instructions at 65° C. in the presence of formamide (50%). Membranes were washed at 65° C. in 2×X sodium chloride, sodium phosphate, EDTA (SSPE) 0.1% SDS. Hybridising plaques were re-screened at densities of 50–100 plaques/plate. Individual plaques hybridising in a 2nd round were cored from the plate, rescued into SM buffer with chloroform, and phage inserts isolated by PCR from boiled aliquots of each coring. Inserts of varying sizes were visualised on a 1XTAE gel. A Southern blot of the gel probed with the 164 bp fragment showed strong hybridisation to a phage insert of 1.7 kb. Plasmids were isolated from appropriate phage stocks using the in vivo excision procedure (Short et al, *Nucl. Acids Res.*, 16: 7583–7600 (1988). The cDNA containing insert of 1.7 kb was designated pASC66.

Northern Blot Analysis of RNA

10 µg total RNA isolated from various parts of the oilseed rape plant were separated on a (1% agarose/3% formaldehyde/10 mM Na₂HPO₄pH 6.5) denaturing gel. The RNA was transferred onto a nylon membrane (GeneScreen, NEN-Du Pont, UK) using capillary transfer. In accordance with the membrane manufacturers' instructions, a riboprobe was transcribed from pSAC66 using the method outlined in the Promega protocols and applications guide, 2nd edition (1991) p59. Unincorporated radionucleotides were removed with a Biogel P-60 column. The blot was washed at 65° C. in 0.1×SSPE, 0.1% SDS and exposed to KODAK™ X-AR5 film with intensifying screens at −70° C.

DNA Sequencing

Supercoiled plasmid DNA from pSAC66 was isolated by the alkaline-lysis method of Sambrook et al, *Molecular Cloning: A Laboratory Manual* New York, Cold Spring Harbour Laboratory Press (1 989), phenol/chloroform extracted and treated with RNase A (Sigma UK) and precipitated with PEG. Sequence data were obtained using an Applied Biosystems automated sequencer employing Taq dyedeoxy terminators. Initial sequence of SAC66 was derived using pBluescript bacteriophage primer T3 and T7 and subsequently using internal primers.

Isolation of *B. napus* fragment encoding PG by PCR with degenerate primers

First strand cDNA was synthesized from *B. napus* mRNA isolated from the DZ of pods harvested at 40, 45 and 50 DAA. *B. napus* cDNA was used in PCR reactions with degenerate primers whose design was based on multiple sequence alignments of fruit-specific and pollen-specific PGs. Two primers were synthesized in the 5' to 3' direction (P1 and P2) to prime with a polyT primer (OG2) and one in the 3' to 5' direction (P3) for a nested PCR approach with P1.

First round PCR products from *B. napus* cDNA were visible as smears in the appropriate size range for all primer combinations (P1+OG2, P2+OG2 and P1+P3). Gel fragments were excised in the expected product size of each primer combination and the DNA eluted for second round PCR reactions. A band of less than 200 bp was visible in the P1+P3 primed reactions from first round PCR products P1+OG2, i.e. nested PCR. This 164 bp fragment was cloned and the sequence (FIG. 2) (SEQ ID NO:7 ) showed significant homology to other PGs within the database.

Homologous screening of the DZ cDNA library for a clone encoding PG using a PCR product Three plates each containing approximately 40,000 clones from a dehiscence zone cDNA library were screened with the 164 bp fragment derived from the nested PCR approach. Distinct hybridisation plaques were taken through a second round of screening and phage inserts amplified by PCR from boiled aliquots of corings. The largest insert was designated as SAC66 and the phage containing this insert were in vivo excised and plasmid DNA prepared for sequencing.

pSAC66 sequence and amino acid analysis

Both strands of the cDNA were sequenced and the result is shown in FIGS. 1A and 1B. When sequenced, the cDNA was 1657 bp in length (SEQ ID NO:5). The largest open reading frame (ORF) was 1299 nucleotides in length, beginning at position 145. The deduced protein sequence (SEQ ID NO:6) of 433 amino acids has a calculated molecular mass of approximately 45 kDa. At the end of the nucleotide sequence there was a large poly(A) tail that encompassed 18(A) nucleotides. The sequence shows close amino acid homology to other polygalacturonases including that isolated from tomato and kiwifruit.

Spatial and temporal expression of SAC66

Northern analysis revealed that the 1657 bp insert from pSAC66 (SEQ ID NO:5) hybridised to a mRNA of approximately 1.7 kb that increased in expression specifically in the dehiscence zone (DZ) tissue excised from pods 45 or 50 DAA. The process of dehiscence is visible to the naked eye at about 50 DAA. No expression of this mRNA could be seen in non-zone pod tissues.

Genomic Southern analysis of SAC66

Figure 4:
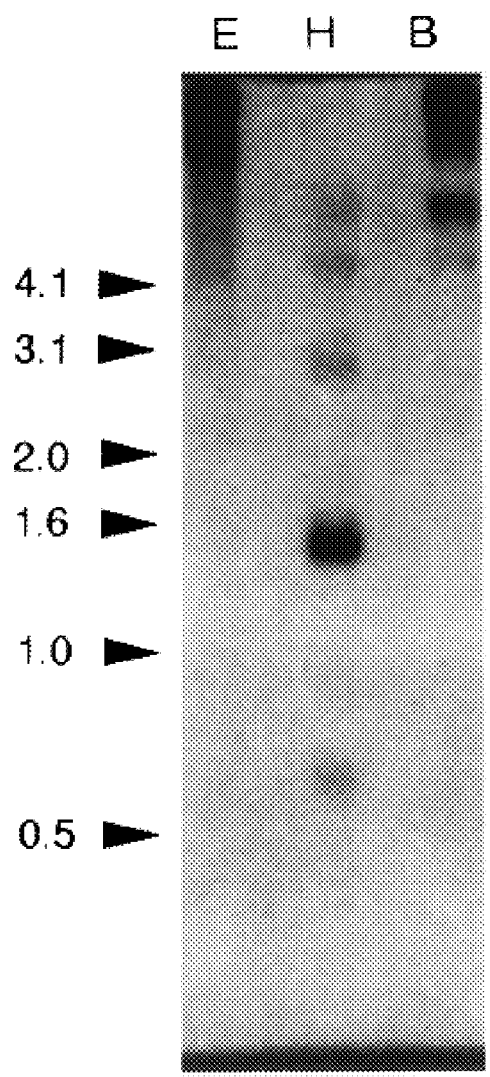
FIG. 4: shows the results of hybridisations using the sequence of FIGS. 1A and 1B (SEQ ID NO:5) of SAC66 to southern blots of *B.napus* genomic DNA digested with EcoRI(E), HindIII(H) and BamHI(B)

The 1657 bp insert of pSAC66 (SEQ ID NO:5) was used as a probe for hybridisation to Southern blots of *B. napus* genomic DNA digested with EcoR1, HindIII and BamH1 (FIG. 4). The probe hybridised to several fragments ranging in size from 12.2 to 0.6 kb. The data suggest that, in this respect, PG is a member of a multi-gene family.

Example 2

Genomic DNA Isolation and Characterisation

DNA was isolated, using a miniprep procedure using a modified form of the extraction buffer described by Clarke et al, *Genome* 3: 334–339 (1989). Young expanding oilseed rape seedlings were homogenised in a 3.8:0.6:0.5 mixture of the following; TNE buffer (0.05 M Tris.HCl pH 7.5, 0.2 M EDTA: 0.1. M NaCl): 5% SDS: 1 mg ml$^{-1}$ proteinase K; to this solution was added sodium diethyldithiocarbamate and sodium bisulphite to 0.4% (w/v) just before use. The samples were then incubated for 1 hr at 37° C. and debris removed by centrifugation in a microfuge at 11,600 g for 5 min. The eluate was then extracted with equal volumes of phenol/chloroform (1:1 v/v) and then chloroform alone. Nucleic acids were then precipitated by the addition of 2.5 vols 95% ethanol containing 5% (v/v) 2 M Na acetate, pH 5.5. The sample was then mixed and immediately centrifuged at 11,600 g for 5 min. The resulting pellet was resuspended in 300 μl TE, 10 μl of RNaseA (10 mg ml$^{-1}$) added, and then incubated at 37° C. for 15 mins before 300 μl CTAB buffer (0.2 M Tris.HCl pH 7.5, 0.05 M EDTA, 2 M NaCl and 2% w/v CTAB) was added before a further incubation at 60° C. for 15 mins. Following re-extraction with an equal volume of chloroform, the DNA was precipitated with an equal volume of isopropanol at −20° C. Subsequent digestions by restriction endonucleases were carried out as detailed in Stacey and Isaac. Restriction enzyme digestion, gel electrophoresis and vacuum blotting of DNA to nylon membranes (1993). The DNA was then separated in 1×TBE, 0.8% agarose and transferred to GENESCREEN+ (NEN) nylon membrane. The SA66 probe was made out according to manufacturers' recommendations. The final wash of the membrane was at 65° C. in 0.1×SSPE 0.1% SDS.

Example 3

RT-PCR

RT-PCR analysis was carried out on oilseed rape pod tissue dissected into DZ and NON-DZ tissue of the pod, embryo, seed coat and funiculus tissues.

Total RNA that had been extracted by the polysomal method, for which the concentration was known, was diluted to 20 ng/μl and 2 μl was used for first strand cDNA synthesis as follows. To 20 ng mRNA or total RNA 1 μl oligo dT (1 mg/ml) and 9.6 μl milli Q water were added. The eppendorf was vortexed, pulsed in a microcentrifuge and incubated at 70° C. for 5 min. After a 5 min cooling period at RT the following were added; 2 μl first strand 10×buffer, 2 μl 10 mM dNTPs (Pharmacia), 2 μl 100 mM DTT (promega), 10 U RNA guard (Pharmacia) and 20 U Stratascript reverse transcriptase (Stratagene UK) and incubated at 37° C. for 30–45 min. The total volume of this reaction mix was 20 μl.

A negative control without reverse transcriptase was included to check for the presence of DNA in the RNA stock.

2 μl of this first strand DNA was then used in a PCR reaction as follows: the PCR reaction contained a final concentration of 1×PCR buffer, 1.5 U Taq polymerase (Promega), 4 μg each of two SAC66 specific primers F1 and R6 which bind to the N' terminal region of SAC66, and 2 μl first strand cDNA in a total volume of 20 μl and was overlaid with mineral oil (Sigma). PCR was carried out in accordance with the following cycles:

| | | |
|---|---|---|
| 1st programme-1 cycle | 95° C. | 5 min |
| | 50° C. | 3 min |
| | 72° C. | 3 min |
| 2nd programme-30 cycles | 94° C. | 1 min |
| | 50° C. | 2 min |
| | 72° C. | 2 min |
| 3rd programme-1 cycle | 94° C. | 2 min |
| | 50° C. | 3 min |
| | 72° C. | 15 min |

A positive control of first strand DNA generated from 40 ng mRNA extracted from the DZ tissue of oilseed rape pods 40, 45 and 50 DAA (as used for the library), first strand cDNA controls without reverse transcriptase and negative PCR controls without DNA were included.

Loading buffer (2 μl) was added to the completed PCR reactions and then 10 μl was run on a 2% agarose gel. To establish the nature of the band produced during PCR the gel was blotted and probed with a SAC66 cDNA insert.

Total RNA was also extracted from seed coat, funiculus and embryo tissues in addition to combined DZ and NON-Z regions of the pod wall by the small scale RNA method. RNase free DNase (1 μl) was added to the RNA in a final concentration of 40 mM Tris-HCl pH 7.5, 6 mM MgCl$_2$ and final volume of 50 μl. The mixture was incubated at 37° C. for 10 min and then phenol:chloroform extracted twice. RNA was precipitated with 0.1 volumes 3 M NaAc pH 6 and 2.5 volumes 100% ethanol and resuspended in 20 μl milliQ water. First strand cDNA synthesis and PCR reactions were carried out as detailed above. However, since it was not possible to quantify the yield of RNA obtained from the small scale preparation it was necessary to amplify the constitutively expressed 25S ribosomal RNA gene in the PCR reactions to ensure that RNA was present and first strand cDNA had been synthesised.

Results

Figure 5A:
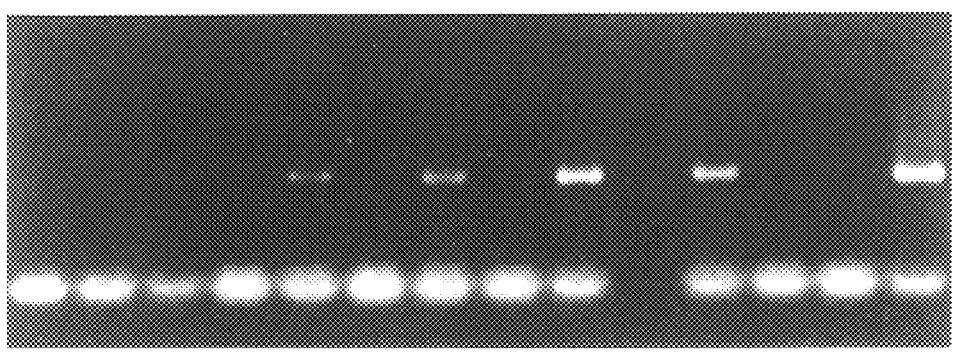
FIGS. 5A–5B: show the results of RT-PCR analysis of RNA extracted from the dehiscence zone (A) and non-zone tissues (B)
Figure 5B:
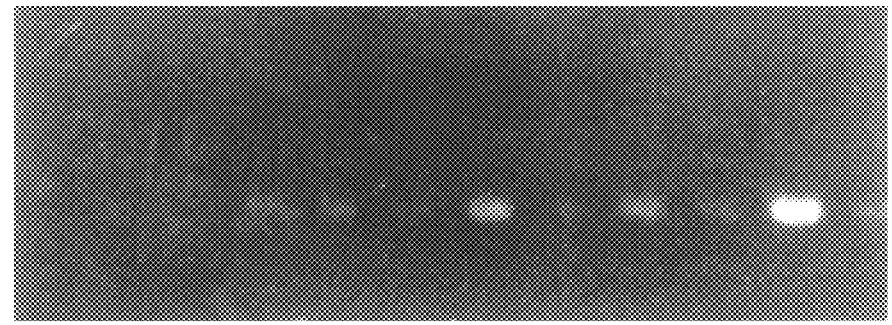
Figure 6:
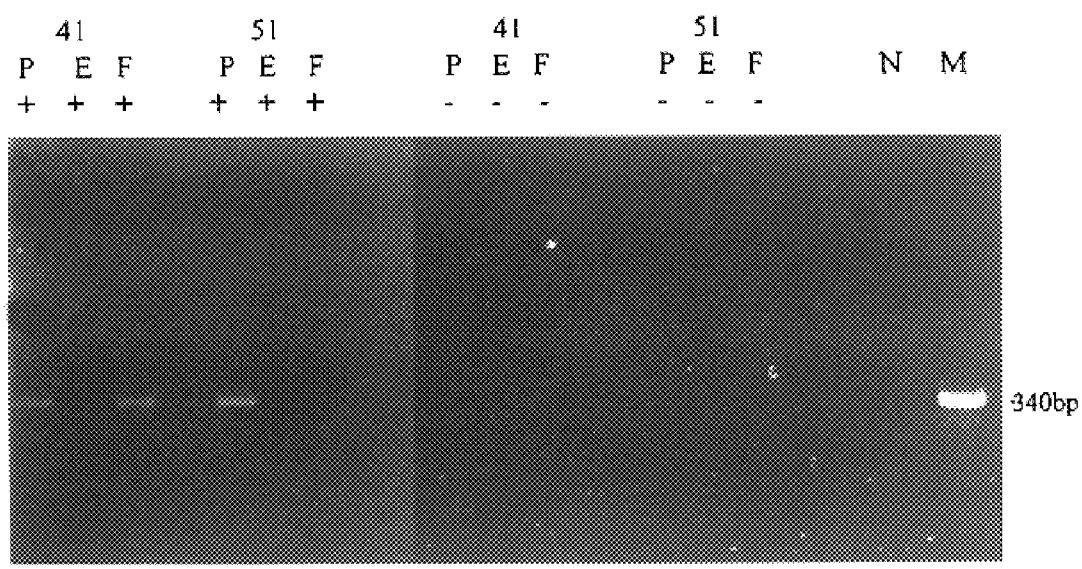
FIG. 6: shows the results of RT-PCR analysis of RNA extracted from embryo (E) and funiculus tissues (F) as well as combined DZ and NON-Z regions of the pod wall valves from *B.napus*.

Agarose gel electrophoresis results of the RT-PCR products are shown in FIGS. 5A, 5B and 6. FIGS. 5A and 5B show that SAC66 mRNA clearly accumulates in the dehiscence zone prior to dehiscence and that no such accumulation occurs in non-zone tissues. In FIG. 6 it can be seen that SAC66 message is localised to pod wall valves and funiculus tissue.

Example 4

Ribonuclease Protection Assays

SAC66 plasmid was prepared as described hereinabove. The plasmid was linearized with Vspl which cuts once in the SAC66 sequence at position 1067 bp and also restricts at position 2218 bp in pBluescript vector sequence to produce a fragment of 2 Kb. The restriction digest was run on a 1% agarose gel and DNA from the 2 Kb fragment eluted using the Geneclean method. The eluted DNA was ethanol precipitated, washed in 70% ethanol and resuspended in milliQ water to a 5 μg/μl concentration.

The 2 Kb fragment (1 μg) was labelled with 2 μl $^{32}$P rUTP in a reaction mix containing 1 μl DTT (100 mM), 2 μl 5×buffer (200 mM Tris-HCl pH 7.5, 30 mM MgCl$_2$, 10 mM spermidine, 50 mM NaCl), 2 μl nucleotide mix containing 2.5 mM each of rCTP, rATP rGTP, 1 μl rUTP (100 μM), 20 U RNase Guard and 1 μl T7 RNA polymerase. The T7 RNA polymerase synthesised a 66 bp antisense strand to the 3' region of SAC66 from the pBluescript T7 promoter site which was present in the 2 Kb fragment. The reaction was incubated at room temperature for 30 min and then 10 U RQ1 DNase was added and incubated at 37° C. for 15 min to digest the DNA template. Loading dye (10 μl of 80% formamide, 10 mM EDTA, 0.1% bromophenol blue, 0.1% xylene cyanol, 0.1% SDS) was added and the samples placed in a 65° C. heating block for 5 min. The samples were run on a 5% acrylamide protein gel (Longranger) in 0.5× BBEbuffer at 250V.

When electrophoresis was complete the gel was briefly exposed to film (4 min). The autoradiograph was used to determine the position of the full length probe which was excised and eluted overnight at 37° C. in 500 μl elution buffer (0.5 M ammonium acetate, 1 mM EDTA and 0.2% SDS).

The following day the supernatant containing the eluted probe was transferred to a fresh tube and diluted with milliQ water until a 20 μl aliquot contained approximately 50 cps. The probe (20 μl) was added to total RNA (10 μg) samples and then both the RNA and probe were precipitated with 0.1 volume 3 M NaAC and 2.5 volumes ethanol at −20° C. for 20 min.

Digested and undigested controls were included containing a similar quantity of yeast tRNA. The digested control will show the efficiency of RNase One to digest single stranded RNA and the undigested control shows that the probe was added to excess.

After centrifugation at 13,000 rpm for 5 min, ethanol was removed and the pellet allowed to air dry before being resuspended in 30 μl hybridization buffer (80% deionized formamide, 40 mM PIPES pH 6.4, 0.4 M NaAc, 1 mM EDTA). The samples were heated to 80° C. for 5 min to denature the RNAs and then hybridized overnight at 42° C.

On the subsequent day 30 μl of the hybridization mix was added to 300 μl RNase digestion buffer (10 mM Tris-HCL pH 7.5, 5 mM EDTA, 2 mM NaAC) containing 2 μl RNase One and incubated at 37° C. for 2 h. To the undigested control only RNase digestion buffer was added. The reaction was terminated by adding 3.3 μl SDS (10%). Yeast tRNA (20 μl) was added to help precipitation of the RNA with 2.5 volumes ethanol. After centrifugation the resulting pellet was air-dried and resuspended in 6 μl loading buffer (80% formamide, 10 mM EDTA, 0.1% bromophenol blue, 0.1% xylene cyanol, 0.1% SDS). The samples were heated to 85° C. for 5 min before loading onto a pre-warmed sequencing gel. A 5% acrylamide sequencing gel was prepared as detailed in the Longranger manual. To the final volume of 50 ml, 150 μl AMPS and 60 μl TEMED were added to generate the polymerization of the acrylamide. The gel was run at approximately 50 W to maintain the temperature of the plates at 50° C. When electrophoresis was complete the gel was transferred to 3 MM paper and dried at 80° C. for 50 min. The dried gel was exposed to film for 20 h at −70° C.

Results

Figure 7:
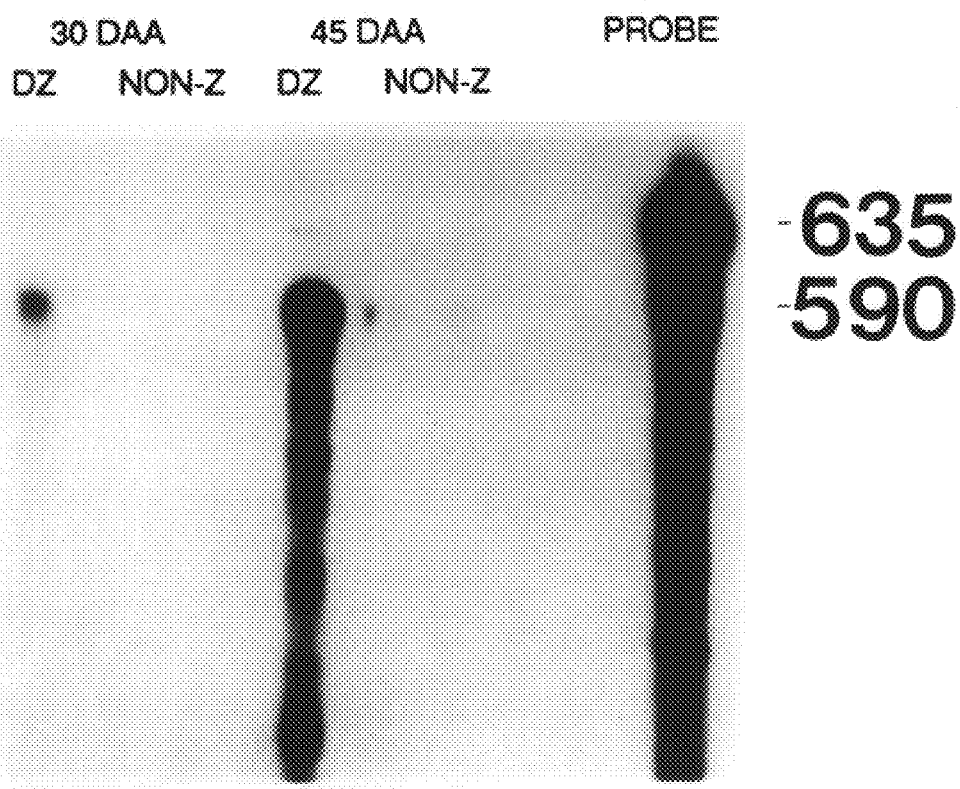
FIG. 7: shows the results of the Ribonuclease protection assay described in example 3.

The results of the Ribonuclease Protection Assay are shown in FIG. 7.

It can be se that this confirms that SAC66 transcript accumulates in the dehisence zone, with no such accumulation occurring in non-zone tissues.

Example 5

Use of SAC66 Promoters

A promoter fragment has been isolated from an Arabidopsis genomic library. PG Southern analysis has indicated that this gene is a single copy in Arabidopsis and possibly two copies in B.napus (FIG. 4).

To demonstrate that the putative promoter region of SAC66 is capable of driving the expression of a foreign gene in B.napus, transcriptional fusions of the promoters can be made to the E.coli gene encoding B-glucuronidase (GUS). Fragments of the clones containing the putative promoter region are subcloned into pB1101 (Jefferson et al, *EMBRO J.,* 6:3901 (1987)). The GUS constructs are then transformed into B.napus using standard transformation techniques. Analysis of the transformed plants demonstrates that GUS activity is preferentially found in the pod shatter zone.

This promoter may then be used to drive other genes including antisense nucleic acid to SAC66 itself. The utility of the SAC66 promoter could also be harnessed by expressing gene fusions to barnase, or other genes that disrupt cellular development or otherwise interfere in the function of the shatter zone in pod shatter, in transgenic plants. Use of the barnase gene to cause cell ablation has been described in EP-A-0344029 and WO-A-9211379, particularly at pages 28 and 29 of the latter document. Transcriptional or translational fusion of the promoter fragments and the transfer of these genes into B.napus plants results in ablation of the pod shatter zone causing shatter-resistance.

Example 6

The construction of Expression Cassettes and their use in Producing Sense and Antisense RNA to Pod Shatter Zone-Specific Messages in transgenic Plants Either pod shatter zone-specific or constitutive promoters can be used to drive expression of sense or anti-sense RNA corresponding to shatter zone-specific transcripts in transgenic plants, thus potentially creating pod mutations and shatter-resistance (indehisence). The same pod shatter zone-specific promoters can be used to drive the pod shatter zone expression of genes encoding proteins or enzymes detrimental to shatter-zone function thereby creating shatter resistance (see previous example). Chimeric genes that can be constructed to produce shatter-resistance include Pea plastocyanin promoter linked to the coding region of the SAC66 cDNA or gene such that sense or antisense SAC66 RNA is produced (see FIG. 8).

Any other suitable promoter may be used. The plasmids may also carry the npt 11 gene which confers resistance to the antibiotic Kanamycin enabling transgenic plants to be selected on Kanamycin containing media. These plasmids are transformed into B.napus using standard Agrobacterium based methods as described in the art (Moloney et al, *Plant Cell reports,* 8:238–242 (1989)). Accumulation of expression of the dehisence-zone specific polygalacturonase enzyme results in oilseed rape with pods which are resistant to shattering.

What is claimed is:

1. A method for controlling dehiscence in a plant in need thereof which comprises transforming a plant or plant propagating material with a dehiscence-controlling amount of a recombinant or isolated nucleic acid sequence encoding an amino acid sequence comprising SEQ ID NO:8, wherein the amino acid sequence is an amino acid sequence of the enzyme polygalacturonase.

2. The method as claimed in claim 1, wherein the polygalacturonase is preferentially or specifically expressed in the dehiscence zone of pericarp tissue.

3. The method as claimed in claim 2, wherein the pericarp tissue is from the genus Brassica.

4. The method as claimed in claim 3, wherein the pericarp tissue is from *Brassica napus*.

5. The method as claimed in claim 1, wherein the nucleic acid sequence is that shown in FIG. 1 (SEQ ID NO:5), or a sequence which hybridizes under stringent conditions to the complement of the nucleic acid sequence of FIG. 1 (SEQ ID NO:5).

6. The method as claimed in claim 1, wherein the nucleic acid sequence further comprises a promoter which naturally controls expression of polygalacturonase.

7. The method as claimed in claim 1, wherein the nucleic acid sequence further comprises a promoter which comprises one or more regulatory elements from a promoter which naturally controls expression of polygalacturonase.

8. A method for controlling dehiscence in a plant which comprises transforming a plant or plant propagating material with a dehiscence-controlling amount of a nucleic acid sequence which is antisense to a nucleic acid sequence encoding an amino acid sequence comprising SEQ ID NO:8, wherein the amino acid sequence is an amino acid sequence of the enzyme polygalacturonase.

9. The method as claimed in claim 8, wherein the antisense nucleic acid sequence is downstream from a promoter.

10. The method as claimed in claim 9, wherein the promoter is a constitutive promoter or a promoter which naturally controls expression of polygalacturonase.

11. A method for regulating dehiscence in a plant in need thereof which comprises transforming a plant or plant propagating material with a dehiscence-regulating amount of a recombinant or isolated nucleic acid sequence encoding an amino acid sequence comprising SEQ ID NO:8, wherein the amino acid sequence is an amino acid sequence of the enzyme polygalacturonase.

12. A method for regulating dehiscence in a plant which comprises transforming a plant or plant propagating material with a dehiscence-regulating amount of a nucleic acid sequence which is antisense to a nucleic acid sequence encoding an amino acid sequence comprising SEQ ID NO:8, wherein the amino acid sequence is an amino acid sequence of the enzyme polygalacturonase.

13. The method as claimed in claim 12, wherein the antisense nucleic acid sequence is downstream from a promoter.

14. The method as claimed in claim 13, wherein the promoter is a constitutive promoter or a promoter which naturally controls expression of polygalacturonase.

15. A transgenic plant comprising a nucleic acid sequence encoding an amino acid sequence comprising SEQ ID NO:8, wherein the amino acid sequence is an amino acid sequence of the enzyme polygalacturonase.

16. Propagating material derived from a plant as defined in claim 15.

17. Seeds derived from a plant as defined in claim 15.

18. A transgenic plant cell which comprises a nucleic acid sequence encoding an amino acid sequence comprising SEQ ID NO: 8 wherein the amino acid sequence is an amino acid sequence of the enzyme polygalacturonase.

19. A recombinant nucleic acid molecule comprising a promoter which naturally controls expression of a nucleic acid sequence comprising SEQ ID NO:5, or a nucleic acid sequence which hybridizes under stringent conditions to the complement of the nucleic acid sequence of SEQ ID NO: 5, wherein the nucleic acid sequence encodes the enzyme polygalacturonase.

20. A transgenic plant comprising a nucleic acid molecule as defined in claim 19.

21. Propagating material derived from a plant as defined in claim 20.

22. Seeds derived from a plant as defined in claim 20.

23. A plant cell which comprises a nucleic acid molecule as defined in claim 19.

24. A method of controlling dehiscence in a plant which comprises transforming a plant or plant propagating material with a dehiscence-controlling amount of the recombinant nucleic acid molecule as defined in claim 19.

25. The method as claimed in claim 24, wherein the promoter drives expression of polygalacturonase in the dehiscence zone of pericarp tissue.

26. The method as claimed in claim 25, wherein the pericarp tissue is from the genus Brassica.

27. The method as claimed in claim 26, wherein the pericarp tissue is from *Brassica napus*.

28. The method as claimed in claim 24, wherein the recombinant nucleic acid molecule further comprises the nucleic acid sequence shown in FIG. 1 (SEQ ID NO: 5), or a sequence which hybridizes under stringent conditions to the complement of the nucleic acid sequence of FIG. 1 (SEQ ID NO:5).

29. A method for regulating dehiscence in a plant which comprises transforming a plant or plant propagating material with a dehiscence-regulating amount of the recombinant nucleic acid molecule as defined in claim 19.

30. The transgenic plant of claim 15, wherein the nucleic acid sequence encodes an amino acid sequence comprising SEQ ID NO:6.

31. The transgenic plant cell of claim 18, wherein the nucleic acid sequence encodes an amino acid sequence comprising SEQ ID NO:6.

32. The recombinant nucleic acid molecule of claim 19, wherein the nucleic acid sequence encodes an amino acid sequence comprising SEQ ID NO:6.

33. A transgenic oilseed rape plant which is shatter resistant, transformed with a nucleic acid sequence which comprises a nucleic acid sequence encoding an amino acid sequence comprising SEQ ID NO:8, wherein the amino acid sequence is an amino acid sequence of the enzyme polygalacturonase.

34. A method for controlling dehiscence in a plant which comprises transforming a plant or plant propagating material with a dehiscence-controlling amount of a nucleic acid sequence which is antisense to SEQ ID NO:5 encoding the enzyme polygalacturonase or to a sequence which hybridizes under stringent conditions to the complement of SEQ ID NO:5 encoding the enzyme polygalacturonase.

35. The method of claim 8, wherein the nucleic acid sequence is antisense to the sequence shown in FIG. 1 (SEQ ID NO:5) or to a sequence which hybridizes under stringent conditions to the complement of the sequence of FIG. 1 (SEQ ID NO:5).

36. A transgenic plant comprising a nucleic acid sequence which is antisense to a nucleic acid sequence encoding an amino acid sequence comprising SEQ ID NO:8, wherein the amino acid sequence is an amino acid sequence of the enzyme polygalacturonase.

37. Propagating material derived from a plant according to claim 36.

38. Seeds derived from a plant according to claim 36.

39. A transgenic plant cell comprising a nucleic acid sequence which is antisense to a nucleic acid sequence encoding an amino acid sequence comprising SEQ ID NO:8, wherein the amino acid sequence is an amino acid sequence of the enzyme polygalacturonase.

40. A transgenic oilseed rape plant which is shatter resistant, transformed with a nucleic acid which comprises a nucleic acid sequence which is antisense to a nucleic acid sequence encoding an amino acid sequence of SEQ ID NO:8, wherein the amino acid sequence is an amino acid sequence of the enzyme polygalacturonase.

41. The method as claimed in claim 24, wherein the recombinant nucleic acid molecule further comprises a nucleic acid sequence which is antisense to the nucleic acid sequence of SEQ ID NO:5, or to a sequence which hybridizes under stringent conditions to the complement of the nucleic acid sequence of SEQ ID NO:5.

42. The method as claimed in claim 29, wherein the recombinant nucleic acid molecule further comprises a nucleic acid sequence which is antisense to the nucleic acid sequence of SEQ ID NO:5, or to a sequence which hybridizes under stringent conditions to the complement of the nucleic acid sequence of SEQ ID NO:5.

43. The method as claimed in claim 29, wherein the recombinant nucleic acid molecule further comprises the nucleic acid sequence shown in SEQ ID NO:5, or a sequence which hybridizes under stringent conditions to the complement of the nucleic acid sequence of SEQ ID NO:5.

* * * * *